(12) United States Patent
Hanson

(10) Patent No.: US 6,955,787 B1
(45) Date of Patent: Oct. 18, 2005

(54) INTEGRATED BIOLOGICAL AND CHEMICAL SENSORS

(76) Inventor: William Paynter Hanson, 1107 Sherwood Dr., Carlisle, PA (US) 17013

( * ) Notice: Subject to any disclaimer, the term of this patent is extended or adjusted under 35 U.S.C. 154(b) by 0 days.

(21) Appl. No.: 10/684,301

(22) Filed: Oct. 11, 2003

(51) Int. Cl.[7] ...................... G01N 21/00; G01N 31/22; G01N 15/06; G01N 33/00; G01N 33/48
(52) U.S. Cl. .......................... 422/50; 422/56; 422/57; 422/68.1; 422/82.01; 422/82.02; 422/83; 422/88; 422/98; 436/43; 436/63; 436/147; 436/149; 436/150; 436/155; 436/151; 73/1.01; 73/1.02; 73/1.82; 73/1.83; 73/23.2; 73/53.01; 73/54.41; 73/61.49; 73/570; 73/579; 29/592; 29/592.1; 29/594
(58) Field of Search .............................. 422/50, 56, 57, 422/68.1, 82.01, 82.02, 83, 88, 98; 436/43, 436/63, 147, 149, 150, 151; 73/1.01, 1.02, 73/1.82, 1.83, 23.2, 53.01, 54.41, 61.49, 73/570, 579; 29/592, 592.1, 594

(56) References Cited

U.S. PATENT DOCUMENTS

| | | | |
|---|---|---|---|
| 3,164,004 A | | 1/1965 | King |
| 4,748,367 A | * | 5/1988 | Bloch et al. ................. 310/343 |
| 5,065,140 A | * | 11/1991 | Neuburger ................... 340/634 |
| 5,411,709 A | * | 5/1995 | Furuki et al. ................. 422/91 |
| 5,696,422 A | | 12/1997 | Hanson |
| 5,744,902 A | | 4/1998 | Vig |
| 5,852,229 A | | 12/1998 | Josse et al. |
| 5,936,150 A | | 8/1999 | Kobrin et al. |
| 5,992,215 A | * | 11/1999 | Caron et al. ................. 73/24.01 |
| 6,044,332 A | | 3/2000 | Korsah et al. |
| 6,076,406 A | | 6/2000 | Blair et al. |
| 6,085,576 A | | 7/2000 | Sunshine et al. |
| 6,293,136 B1 | | 9/2001 | Kim |
| 6,379,623 B1 | * | 4/2002 | Mays, Jr. ................. 422/82.08 |
| 6,432,362 B1 | | 8/2002 | Shinar et al. |

* cited by examiner

*Primary Examiner*—Jill Warden
*Assistant Examiner*—Brian Sines
(74) *Attorney, Agent, or Firm*—Mary J. Gaskin

(57) ABSTRACT

An array of piezoelectric resonators used in a sensor device in order to identify chemical and biological agents. The resonators can operate as bulk acoustic wave (BAW), surface acoustic wave (SAW), or Love mode devices. The sensor device integrates gravimetric, calorimetric, thermal gravimetric, voltage gravimetric and optical detection methods into one sensor system, improving the accuracy of identifying hazardous agents. For gravimetric detection, dual-mode resonators provide simultaneous calorimetric and gravimetric data, one type from each mode. Resonators with heaters on the surfaces will provide thermal gravimetric data. An optical detector can be used to analyze the optical signal from the surface of a coated resonator. Additionally, voltage gravimetric measurements can be made with an electric field set up between the resonator and an external electrode. Thermal voltage gravimetric measurements can be made by adding an integrated heater on the resonator with an external electrode. An alarm can be activated upon the identification of a hazardous agent. The sensor device can utilize other valuable information, including traceable time, GPS location, and variables related to temperature, humidity, air speed, and air direction.

19 Claims, 6 Drawing Sheets

INTEGRATED BIOLOGICAL AND CHEMICAL SENSORS

FIELD OF THE INVENTION

The present invention relates to biological and chemical sensors integrating several physical measurements of target agents.

BACKGROUND OF THE INVENTION

The fast and accurate identification of biological and chemical agents is not only of great interest within the sensor community, but performs a public service by saving lives. The wide dissemination of inexpensive and accurate sensor systems with very low or zero false alarm rates is critical in order to respond to terrorist threats or accidental exposures. False alarms are very costly and could lead to dilatory responses to subsequent real terrorist threats and accidental exposures.

The effectiveness of the first responders depends upon their knowing what hazardous substance has been detected, the concentration of the hazardous substance and the time of the initial exposure. A sensor system which is fast, inexpensive and accurate, and with a low false alarm rate, is critical in both military and civilian applications.

The false alarm rate can be reduced significantly through the use of multiple orthogonal detection methods. Orthogonal methods detect different physical characteristics of a target agent or substance. For example, optical and gravimetric effects are orthogonal. Gravimetric effects result from mass changes on the resonator, while optical techniques look at the interaction of electromagnetic radiation.

For example, U.S. Pat. No. 5,744,902 to Vig describes detectors using a dual-mode sensor using both a gravimetric and a calorimetric analysis of chemical/biological agents.

However, other than gravimetric and calorimetric, none of the prior art detection systems integrates two or more orthogonal measurements (selected from the following methods: gravimetric, calorimetric, thermal gravimetric, voltage gravimetric, and optical detection methods) into one sensor system, thereby substantially improving the identification of hazardous agents and reducing the false alarm rate.

SUMMARY OF THE INVENTION

The present invention provides an array of piezoelectric resonators, which are used as a "laboratory" for measuring mechanical, physical and chemical effects. The array can be manufactured from a single resonator, or individual resonators can be formed into an array, depending on the application.

The resonators in the array can be arranged into configurations for each test. For gravimetric detection, dual-mode resonators will provide simultaneous calorimetric and gravimetric data, one type from each mode. Resonators with heaters on the surfaces will provide thermal gravimetric data. Further, the heaters can make the resonators "self-cleaning." An optical detector can be used to analyze the optical signal from the surface of a coated resonator; incorporating gold-nano particles into the coating and the electrode of the resonator can enhance the optical signal. Additionally, voltage gravimetric measurements can be made with an electric field set up between the resonator and an external electrode. Thermal voltage gravimetric measurements can be made by adding an integrated heater on the resonator with an external electrode.

The array of piezoelectric resonators can operate as bulk acoustic wave (BAW), surface acoustic wave (SAW), or Love mode devices.

The integration of gravimetric, calorimetric, thermal gravimetric and optical analytical methods into one sensor system greatly reduces the false alarm rate for detecting chemical and biological agents. For example, after the optical sensor provides data to identify a target agent, the resonators can be used to determine its concentration.

The sensors can be used in buildings and open spaces to monitor terrorist threats for Homeland Security and to identify hazardous waste in environmental applications. They can be used to monitor chemical and biological agents in military and commercial settings. Further, they can be used to detect toxic mold in buildings.

It is an object of the present invention to provide a sensor system capable of detecting a wide variety of chemical and biological agents and concentrations, with an extremely low false alarm rate.

Another object of the present invention is to combine two or more orthogonal detection methods based on gravimetric, calorimetric, thermal gravimetric, voltage gravimetric, and optical measurements.

Still another object of the present invention is to provide a sensor system which is fast and accurate, yet inexpensive.

DESCRIPTION OF THE PREFERRED EMBODIMENT

Figure 1:
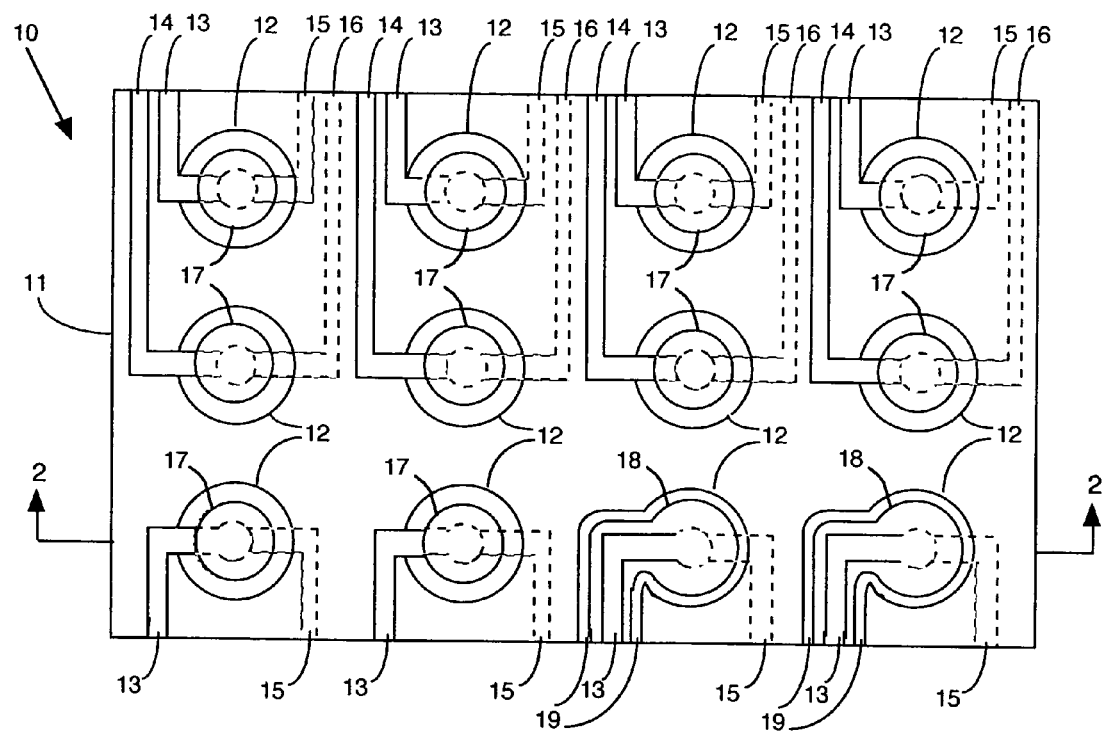
FIG. 1 is a top view of an array of bulk acoustic wave (BAW) devices.

The integrated sensors of the present invention use piezoelectrically-based resonators designed from a piezoelectric crystal such as quartz, lithium niobate, lithium tantalate, langasite, or Gallium Orthophosphate. The resonators can operate as bulk acoustic wave (BAW), surface acoustic wave (SAW), or Love mode devices. In all cases, the frequency is influenced by material deposited onto the surfaces. When mass is deposited onto the crystal, a change in frequency of the resonator occurs.

The sensors are miniature laboratories capable of measuring mechanical, physical and chemical effects. The sensors described herein can be used for detecting the presence and concentration of chemical and biological agents in a medium of air or liquids. A sensor array is formed from a number of resonators, each a multiple (2, 3 or more) mode piezoelectric resonator, which is energy trapped, having a highly smooth surface relative to the wavelength of the mode. Electrodes formed on each resonator excite the resonator. A coating of nano particles (gold, carbon or another material) can be used to enhance the absorption sites for the target agent (and the resonator's gravimetric response), as well as the optical reflectivity for optical detection. A sensor coating on the resonators will bond, chemically or physically, to certain target agents. Each resonator can have a different sensor coating; some can have no coating at all. The different sensor coatings applied to the resonators in an array are selected so that orthogonal physical properties can be measured, thereby allowing the user to look at the target agent from different directions. A heating element on the resonator controls its temperature and is used to generate data for use in thermal-gravimetric analysis (mass change with heat).

Using conventional means, the medium to be tested is concentrated and then delivered to the surface of the crystal resonators. An excitation circuit causes the multiple modes of the resonators to be excited at the same time so that the mass change and temperature change can be measured independently, allowing the mass loading to be calculated accurately. A circuit with variable drive levels can be used to detect when the particles on the surface of the resonator become detached. An optical sensor focused on the surface of the resonator can be used to identify the atomic absorption wavelengths of the target agent. The optical sensor can be transmitted, reflected or fluorescent light. A circuit measures the power dissipated in the crystal via the heating element and can be used to determine the heat of reaction between the target agent and the coating on the surface of the resonator (the additional heat generated in the resonator causes a decrease in the heat required to maintain the crystal at a predetermined temperature). A measurement circuit is used to collect the gravimetric, calorimetric, thermal-gravimetric and optical data. An analysis algorithm is used to determine the identify of the target agent. A communications system is used to relay information about the detected agent and its concentration. Finally, an alarm system can be utilized when the target agent and/or its concentration are identified as hazardous.

As shown in Table 1 below, typically the following physical characteristics can be measured:

TABLE 1

| PHYSICAL CHARACTERISTICS MEASURED | MEASUREMENT | VARIABLE CONTROL PARAMETER |
|---|---|---|
| Gravimetric (mass change) | Frequency of first mode | None |
| Calorimetric (heat generated) | Frequency of first and second mode | None |
| Elastic Properties of film | Impedance of first mode | None |
| Drive Power Effects on Impedance of first mode | Impedance of first mode | Drive Power |
| Drive Power Effects on Frequency of first mode | Frequency of first mode | Drive Power |
| Thermal-Gravimetric (mass change with temperature) | Frequency of first mode vs. temperature of resonator | None |
| Voltage-Gravimetric (mass change with electric field) | Frequency of first mode vs. temperature of resonator | None |

TABLE 1-continued

| PHYSICAL CHARACTERISTICS MEASURED | MEASUREMENT | VARIABLE CONTROL PARAMETER |
|---|---|---|
| Thermal-Voltage Gravimetric (mass change with electric field and temperature) | Frequency of first mode, temperature or resonator, and electric field | Temperature or Voltage |

When enough physical characteristics of a target agent are measured, the accuracy of the identification is greatly increased, resulting in zero or near-zero false alarms. In addition, thresholds can be set to permit certain concentrations of target agents to be tolerated, with an alarm sounding only when the concentration reaches an unacceptable level.

Figure 2:
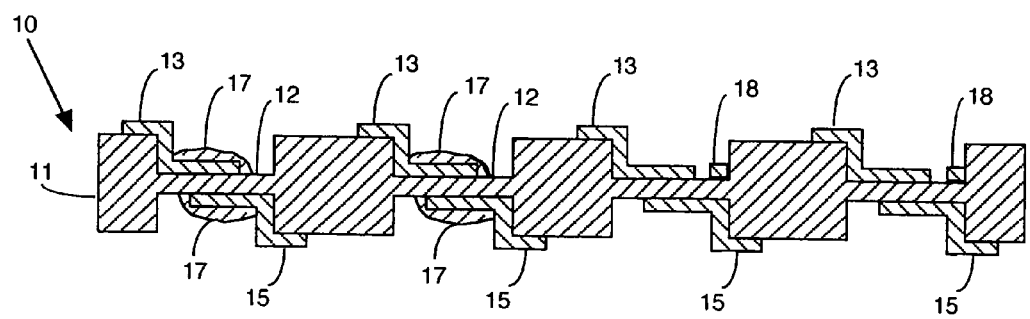
FIG. 2 is a cross-sectional side view of the array of the BAW devices illustrated in FIG. 1 taken along line 2—2.

The present invention can be embodied in a bulk acoustic wave (BAW) array 10, such as the one shown in FIG. 1 and FIG. 2. Formed on a single crystal quartz wafer 11 is an arrangement of BAW resonator plates 12. The BAW resonator plates 12 can be round, as shown, or can have another shape, such as square or hexagonal. The BAW resonator plates 12 can be arrayed in a 3×4 array, as shown, or can be arrayed 2×2, 2×n, 3×3, 3×n, 4×4, or 4×n. The BAW resonator plates 12 have contoured surfaces to improve the short term stability of the resonators by reducing the noise flow.

Depending on its position in the BAW array 10, each BAW resonator has either a top edge electrode 13 or a top center electrode 14 (on the top side of the crystal quartz wafer 11), as well as with a bottom edge electrode 15 or a bottom center electrode 16 (on the bottom side of the crystal quartz wafer 11). The electrodes 13, 14, 15, 16 can be coated with nano particles (e.g., gold) to enhance the absorption of the target agent as well as the optical reflectivity.

Some of the BAW resonator plates 12 will have been coated with a sensor coating 17, the sensor coatings 17 having been collectively designed to differentially absorb to a specific chemical or biological agent, mass loading the resonator and giving off heat in the reaction. The heat of reaction can be detected by operating the resonator on two modes, using one mode which is temperature compensated (changes very little with temperature) and another which has a large temperature coefficient. For example, a BAW resonator operating on the third overtone C mode, designed with minimum frequency shift over the temperature range can be used with a third overtone B mode over the same temperature range designed to have a large frequency shift with temperature. A third overtone C mode, designed with minimum frequency shift over a temperature range, could be used with a fundamental C mode, designed to have a higher frequency shift over the same temperature range.

The material used for each sensor coating 17 can be a metal, metallic alloy, polymer, ceramic, carbon, nano-structure, or gold nano-particle. A different coating 17 can be used on each BAW resonator plate 12 in order to detect different target agents.

The BAW sensor array 10 shown in FIG. 1 and FIG. 2 also shows the integrated heater element 18 on two of the BAW resonator plates 17. The heater element 18 can be used to control the temperature of the BAW resonators. In addition, thermal gravimetric data detectors 19 can be used to monitor the current or voltage through the heater element 18 in order to determine the heat of reaction between the thin film and the target agent; the heat generated in the reaction will decrease the amount of heat required to maintain the resonators at a predetermined temperature. The heater elements 18 can also be used to "self-clean" the resonators and regenerate sensor coatings 17 which have become saturated.

Data collected from the BAW resonator plates 12 includes gravimetric/calorimetric data, thermal-gravimetric data. In addition, information related to the elastic properties of the monolayer can be determined from the loss in the BAW resonators. Further, a circuit with variable drive levels can detect when the particles on the surface become detached.

Figure 3:
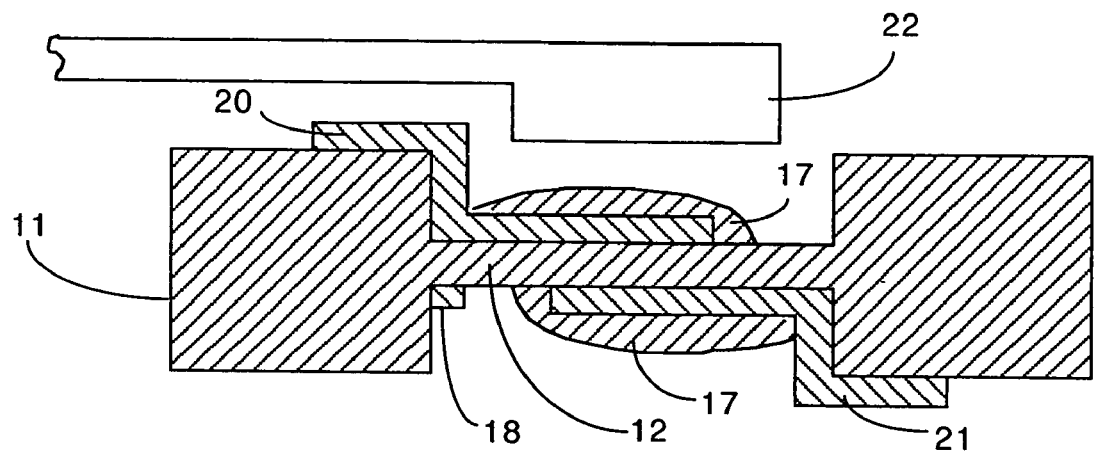
FIG. 3 is a cross-sectional side view of a BAW device, with an external electrode plate.

FIG. 3 shows another embodiment of the present invention. A portion of the crystal quartz wafer 11 has a BAW resonator plate 12, with a top electrode 20 and a bottom electrode 21, which can be coated with nano particles to enhance the absorption of the target agent. The BAW resonator plate 12 has been coated with a sensor coating 17 to bind with a specific chemical or biological agent. A heater element 18 can be used to control the temperature of the BAW resonator plate 12. An external electrode plate 22 has been arranged to set up an electrical field between the top electrode 20 and the external electrode plate 22, which provides for the voltage gravimetric measurement of mass loss with applied electric field.

Figure 4:
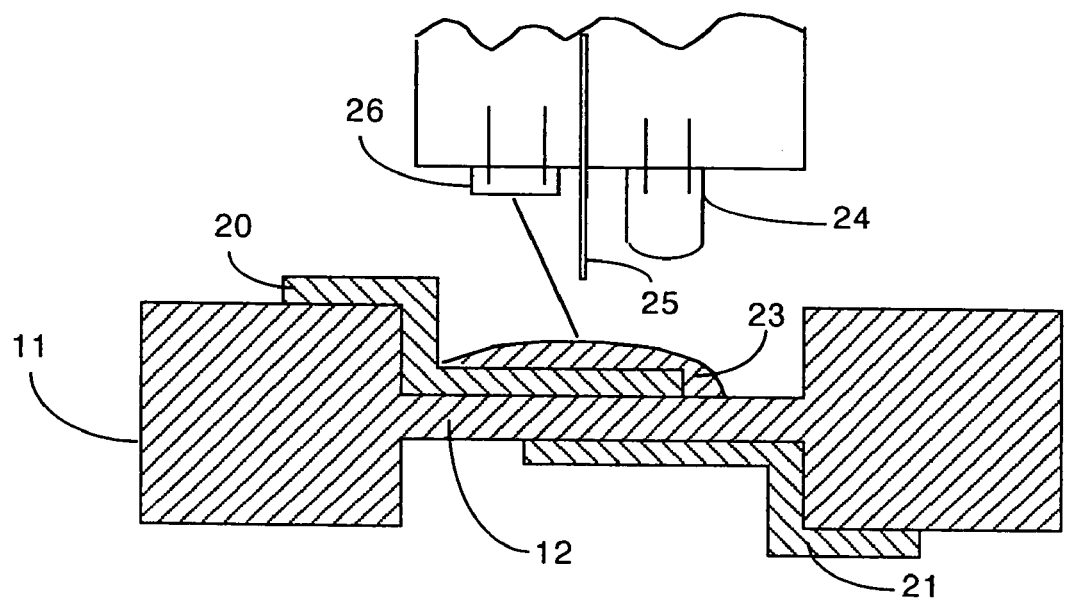
FIG. 4 is a cross-sectional side view of a BAW device integrated with a fluorescent optical detector system.

FIG. 4 shows the present invention integrated with an optical detector. A portion of the crystal quartz wafer 11 has a BAW resonator plate 12 with a top electrode 20 and a bottom electrode 21, which can be coated with nano particles to enhance optical reflectivity. The top electrode 20 on the BAW resonator plate 12 has been coated with a sensor coating 23 which is capable of fluorescing. The optical detector system consists of an optical source 24, such as an organic light emitting diode (OLED), a separation barrier, or shield 25, and an optical detector 26, arranged to detect the fluorescence of biological or chemical agents adsorbed onto the top electrode 20 on the BAW resonator plate 12. The optical detector system is used to identify the atomic absorption wavelengths of the target agent.

The present invention can also be embodied in a surface acoustic wave (SAW) array 27, such as the one shown in FIGS. 5 through 8. A surface acoustic wave device, such as the one shown, is formed from a quartz crystal designed to support high-frequency acoustics oscillators, which are sensitive to surface effects. The SAW array 27 shown in FIG. 5 and FIG. 6 has a surface acoustic wave (SAW) substrate 28. Each SAW resonator has an input electrode 29 and an output electrode 30 coupled to the substrate 28. A sensor coating 32 can cover a portion of the substrate 28 (as shown) or can cover the electrodes 29, 30 and the entire upper planar surface of the substrate 28, so long as the sensor coating 32 material would not corrode the electrodes 29, 30.

The SAW resonator can be arrayed in a 3×4 SAW array 27, as shown, or can be arrayed 2×2, 2×n, 3×3, 3×n, 4×4, or 4×n. The electrodes 29, 30 can be coated with nano particles (e.g., gold) to enhance the absorption of the target agent as well as the optical reflectivity.

Each of the SAW resonators in the SAW array 27 can have a different sensor coating 32 designed to chemically attach to a specific chemical or biological agent, mass loading the resonator and giving off heat in the reaction.

Figure 5:
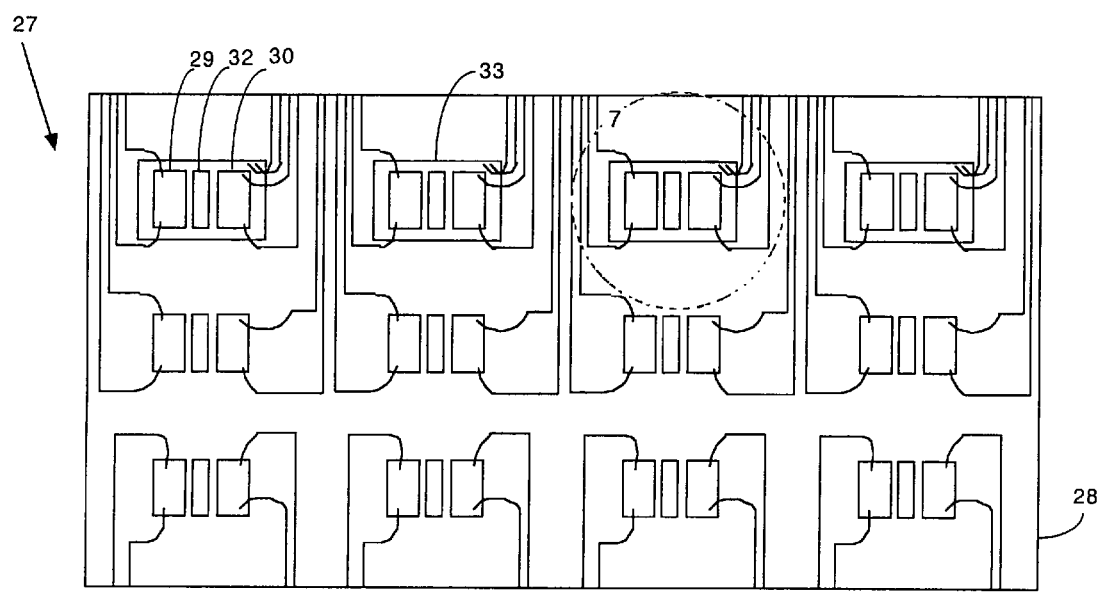
FIG. 5 is a representational top view of an array of SAW devices.
Figure 6:
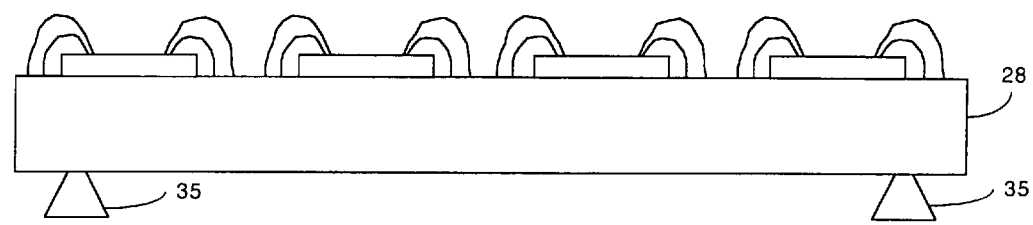
FIG. 6 is a representational side view of the array of SAW devices.

The SAW array 27 shown in FIGS. 5 and 6 has integrated heater elements 33 encircling the electrodes 29, 30 of several of the SAW resonators. The heater elements 33 can be used to control the temperature of the SAW resonators. In addition, the current or voltage through the heater elements 33 can be monitored to determine the heat of reaction, which will decrease the amount of heat required to maintain the resonators at a predetermined temperature. Heat from the heater elements 33 can also be used to "self-clean" the resonators and regenerate sensor coatings 32 which have become saturated.

As shown in FIG. 6, the SAW substrate 28 is thermally insulated by stand-offs 35.

Figure 7:
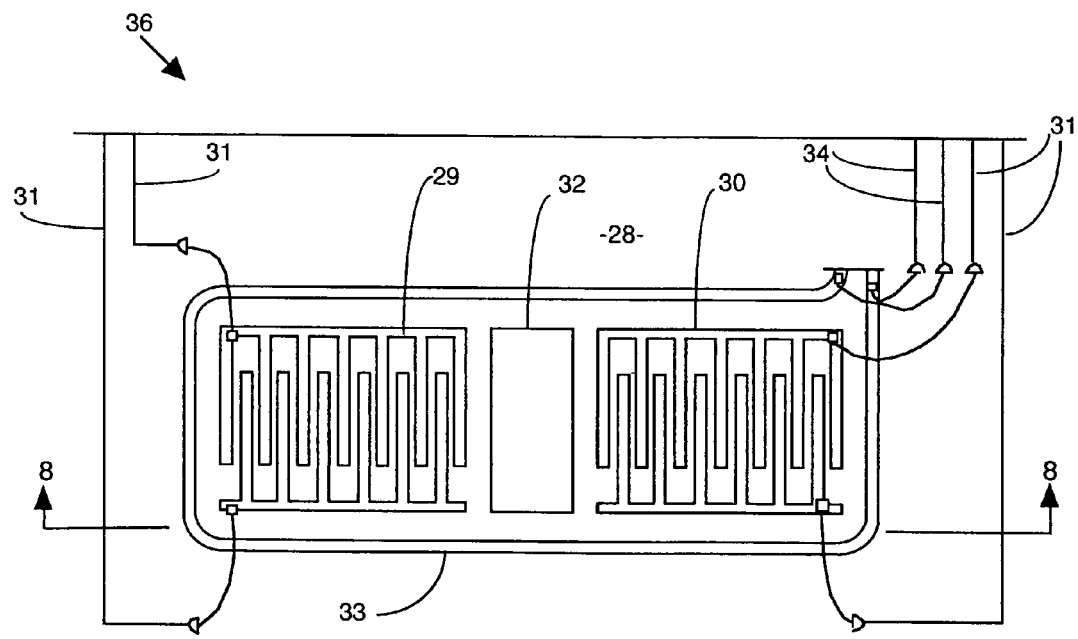
FIG. 7 is a top detail view of a single surface acoustic wave (SAW) device.
Figure 8:
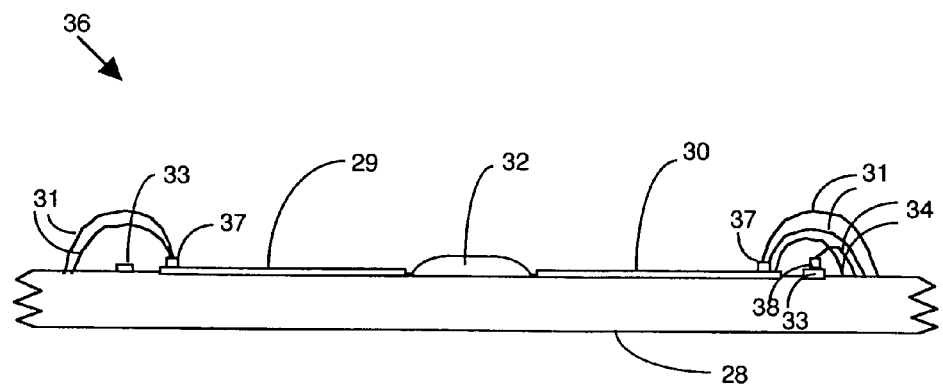
FIG. 8 is a sectional view of the single SAW device illustrated in FIG. 7 taken along line 8—8.

A single SAW resonator 36 is shown in detail in FIG. 7 and FIG. 8. The input electrode 29 and output electrode 30, with a sensor coating 32 in between, are disposed on substrate 28. Electrode wires 31 connect the electrodes 29, 30 to a power source (not shown). Similarly, heater element wires 34 connect the heater element 33 to a power source (not shown). In FIG. 8 the electrode contacts 37 and heater contacts 38 can be seen.

Figure 9:
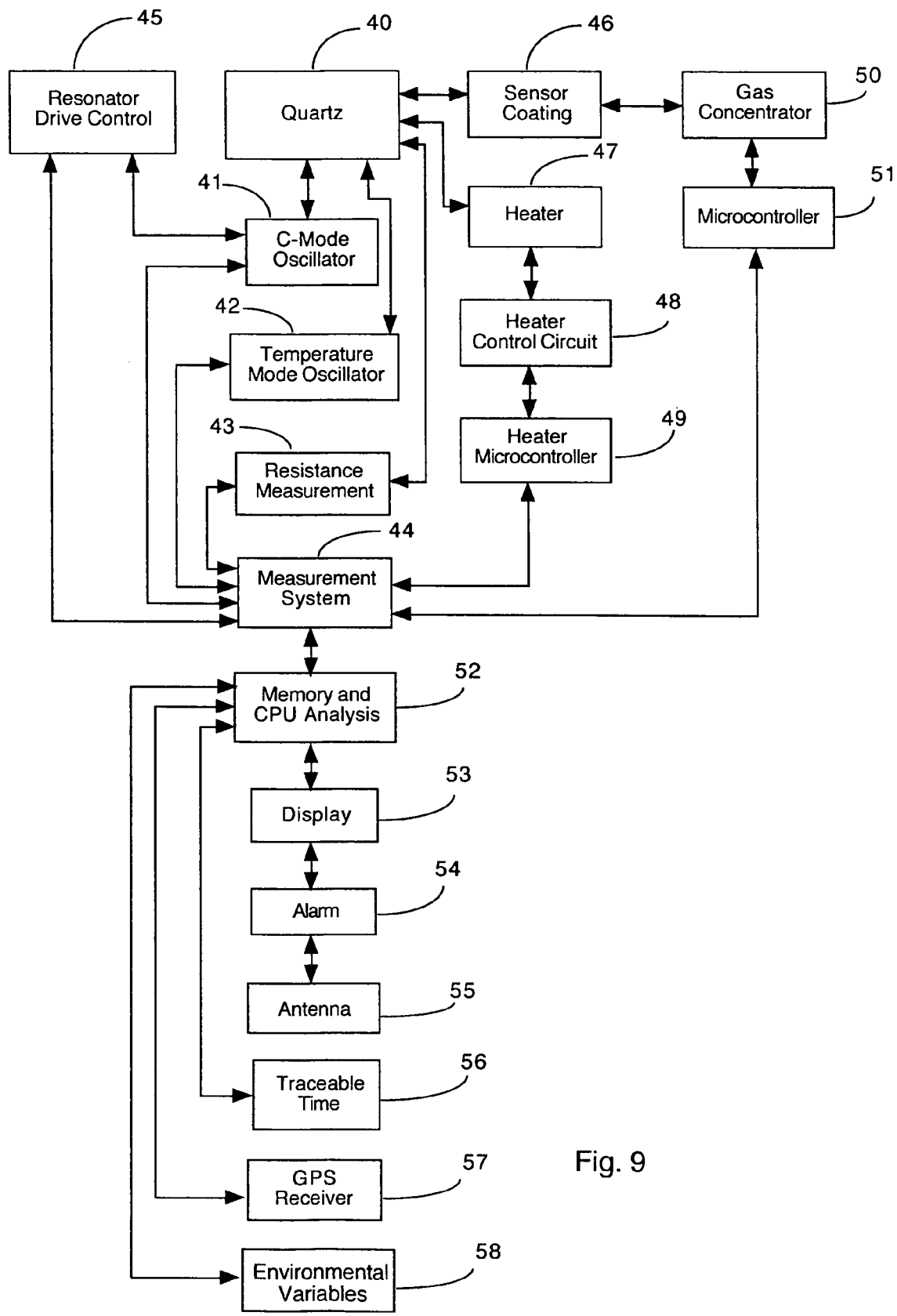
FIG. 9 is a schematic diagram illustrating the sensor device of the present invention.

FIG. 9 is a schematic diagram illustrating the sensor device of the present invention. The quartz resonator 40 is a resonator formed of a piezoelectric material. As noted supra, the resonator can operate as a bulk acoustic wave (BAW), surface acoustic wave (SAW), or Love mode device. The quartz resonator 40 is excited by electrical signals of varying frequency from the C-mode oscillator 41 and the B-mode or other temperature mode oscillator 42. A resistance measurement 43 is delivered to the measurement system 44, as well as data collected from the C-mode oscillator 41 and the temperature mode oscillator 42. The resonator drive control can cause effects on the frequency and impedance of the C-mode oscillator 41, which are transmitted to the measurement system 44. A sensor coating 46 is generally applied to the surface of the quartz resonator 40. A heater 47 can be attached to or embedded in the surface of the quartz resonator 40. A heater control circuit 48 controlled by heater microcontroller 49 affects the temperature of the heater 47, controlling the temperature of the quartz resonator 40; the temperature measurements are transmitted to measurement system 44. A gas concentrator 50, controlled by microcontroller 51, concentrates the target agent and forces it across the surface of the quartz resonator 40.

The data from measurement system 44 is delivered to the memory and CPU 52 for analysis and correlation. The results of the analysis are sent to the display 53 for reading by the operator. An alarm sounds if the target agent and/or its concentration are identified as hazardous. The antenna 55 can be used to transmit the information to a remote location.

The traceable time 56 provides the time (G.M.T.) at which a target agent is being tested. Traceable time, with an accuracy suitable for the application, is critical. In an application where the wind speed could be sixty miles per hour (60 mph), the air is moving at 88 feet per second. Time synchronization within a sensor network must be accurate enough to be usable for predicting the position of a hazardous cloud. Time inaccuracies of 10 seconds in 60 mph wind will lead to errors of 880 feet. Time synchronization using traceable time to 1 millisecond will reduce this error to less than one foot.

The GPS receiver 57 gives the exact location at which the target agent is being tested, detailing the latitude, longitude, and altitude of the test.

Environmental variables 58 provides valuable information relating to such factors as temperature, humidity, wind or air speed, and wind or air direction.

Table 2, below, shows the characteristics measured by the present invention, the measurement means, and the resulting measurements.

TABLE 2

| CHARACTERISTIC MEASURED | MEASUREMENT MEANS | MEASUREMENT |
|---|---|---|
| Gravimetric | From C-mode oscillator | Frequency or voltage |
| Temperature | From B-Mode or other temperature mode oscillator | Frequency or voltage → temperature |
| Resistance (loss) | Resonator peak width | Slope of peak at frequency |
| Drive | Current of crystal | Current or voltage |
| Heater current | Current | Current |
| Time | Clock | Date and time |
| Location | GPS Receiver | Latitude, longitude, altitude |
| Temperature | Thermometer | Degrees |
| Humidity | Barometer | Barometric pressure |
| Air speed and direction | Anemometer | Velocity and direction |

Figure 10:
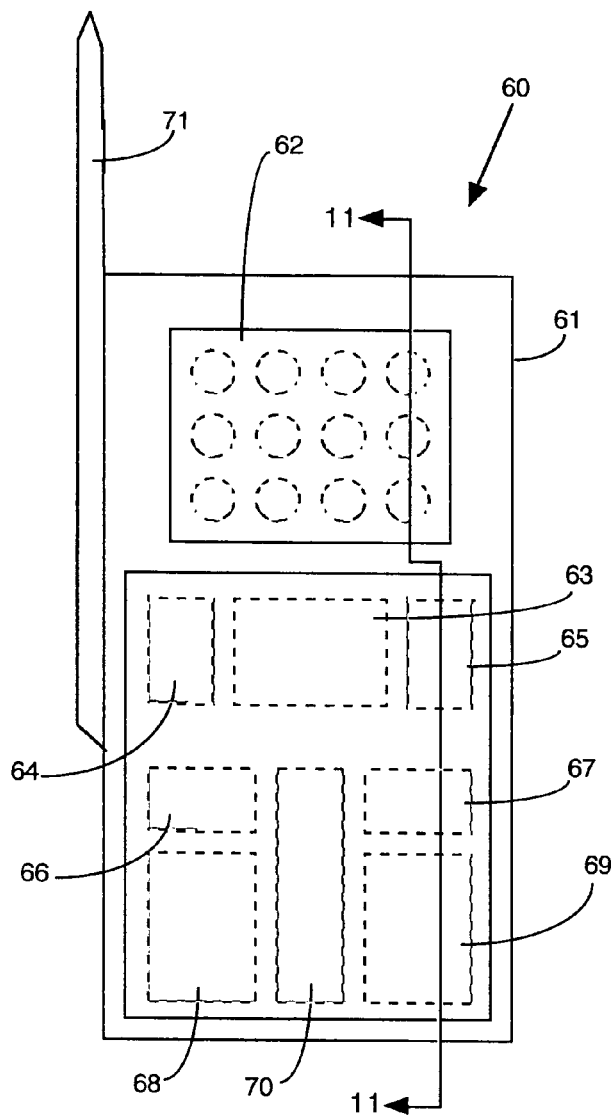
FIG. 10 is a representational top view of the sensor device of the present invention, embodied in a hand-held unit.
Figure 11:
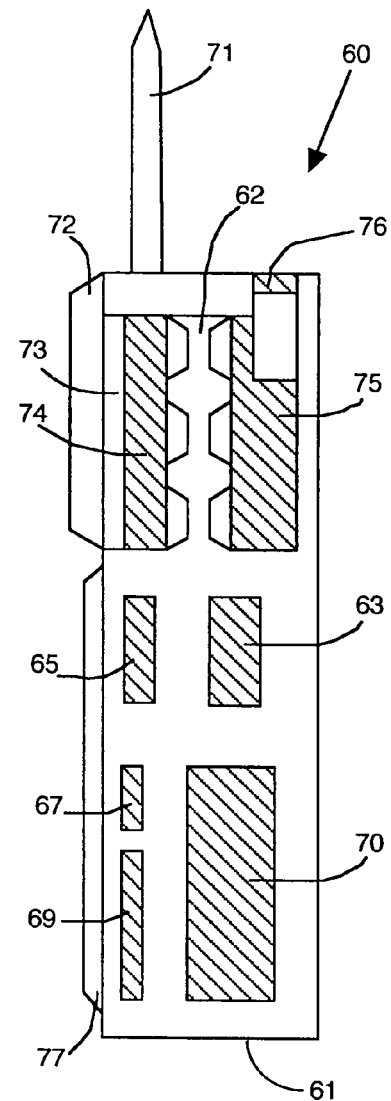
FIG. 11 is a representational cross-sectional side view of the sensor device illustrated in FIG. 10 taken along line 11—11.

FIGS. 10 and 11 show a typical sensor device 60 of the present invention embodied in a hand-held configuration. Disposed within a conventional rectangular housing 61 is the sensor array 62, which can be comprised of piezoelectric-based resonators designed from quartz, lithium, niobate, lithium tantalate, langasite, Gallium Orthophosphate, or any piezoelectric crystal. The resonators (described supra in more detail) in the sensor array 62 can operate as bulk acoustic wave (BAW), surface acoustic wave (SAW), or Love mode devices. The sensor array 62 is connected electronically to the sensor array 63, which generally consists of several circuits, including an excitation circuit for each of the multiple modes; a circuit with variable drive levels; a circuit to provide heat; a circuit used to measure the power dissipated in the crystal via the heater and further used to determine the heat of reaction between the target agent and the coating on the resonator surface; a measurement circuit used to collect data, incurring resonant frequencies and magnitudes of impedance over a frequency range; and an optical sensor. The sensor array electronics 62 are connected to microcontrollers 64, 65, 66, 67 and to the memory 68, 69, which together correlate and characterize the data, comparing, for instance, the sensed frequencies with reference frequencies. A battery 70 provides power for operation of the hand-held embodiment 60. An antenna 71 can be used to transmit data to a remote location.

As shown in FIG. 11, an air-borne target agent is pulled through filter 72 by air pump 73, and is then concentrated by concentrator 74. The target agent has been forced across the sensor array 62, using a piezoelectric fan or MEMS-based fan. Then, a pumping system 75 removes it from the hand-held embodiment 60, forcing it out through exit filter 76. The results of the analysis of the data related to the target agent are shown on the display screen 77.

Although the description contains much specificity, these details should not be construed as limiting the scope of the invention, but merely providing illustrations of some of the presently preferred embodiments of this invention. Thus the scope of the invention should be determined by the appended claims and their legal equivalents, rather than by the examples given.

I claim:

1. An integrated sensor device for use in identifying biological and chemical agents, the sensor device comprising:

(a) an array of piezoelectric resonators having electrodes, each of the resonators operating in a mode selected from the group consisting of a single mode and a dual mode;
(b) two or more different sensor coatings, each one disposed on one of the resonators, the sensor coatings collectively designed to differentially absorb to one or more of the biological and chemical agents for measuring orthogonal physical properties;
(c) one or more heater elements, each one integrated to one of the piezoelectric resonators;
(d) a control circuit for exciting the piezoelectric resonators and for measuring frequency and impedance;
(e) a control circuit configured for varying the temperature of the heater elements and for measuring the temperature, frequency and impedance of the resonators at a plurality of temperatures in order to generate data for use in thermal-gravimetric analysis; and
(f) means for analyzing data collected from the control circuits to identify the biological and chemical agents.

2. The sensor device of claim 1 wherein the piezoelectric resonators are made from a piezoelectric crystal selected from the group consisting of quartz, lithium niobate, lithium tantalate, langasite and gallium orthophosphate.

3. The sensor device of claim 1 wherein the array of piezoelectric resonators can operate as a device selected from the group consisting of a bulk acoustic wave (BAW) device, a surface acoustic wave (SAW) device, and a Love mode device.

4. The sensor device of claim 1 wherein each of the sensor coatings is made from a material selected from the group consisting of metal, metallic alloy, polymer, ceramic, carbon, nano-structure, or gold nano-particles.

5. The sensor device of claim 1 which further includes an external electrode arranged to set up an electrical field between one of the resonators and the external electrode.

6. The sensor device of claim 1 wherein at least one of the sensor coatings disposed on a resonator is capable of fluorescing and which further includes an optical source and an optical detector arranged to probe the fluorescing sensor coating.

7. The sensor device of claim 6 wherein the resonator further includes gold nano panicles.

8. The sensor device of claim 1 which further includes at least one of measurement means selected from the group consisting of a clock, a GPS receiver, a thermometer, a barometer, and an anemometer.

9. The sensor device of claim 1 which further includes an alarm means.

10. A method for identifying biological and chemical agents comprising the steps of:

(a) selecting an array of piezoelectric resonators operating in a mode selected from the group consisting of a single mode and a dual mode, at least one of the resonators having a heater element integrated thereto;
(b) applying a sensor coating to two or more of the resonators, the sensor coatings collectively designed to differentially absorb to one or more of the biological and chemical agents;
(c) exposing the piezoelectric resonators to a substance containing one or more suspected chemical and biological agents;
(d) electrically exciting the piezoelectric resonators;
(e) measuring the frequency and impedance of the piezoelectric resonators;
(f) measuring the temperature of the heater element;
(g) activating the heater element;

(h) controlling the temperature of the heater element at a plurality of temperatures;

(i) measuring the frequency and impedance of the piezoelectric resonators at the plurality of temperatures;

(j) measuring the temperature of the heater element at the plurality of temperatures;

(k) analyzing the data collected from steps (e), (f), (i) and (j);

(l) using the results of step (k) to identify a specific biological or chemical agent.

11. The method of claim 10 wherein the piezoelectric reaonators are made from a piezoelectric crystal selected from the group consisting of quartz, lithium niobate, lithium tantalate, langasite and gallium orthosphosphate.

12. The method of claim 10 wherein the array of piezoelectric resonators can operate as a device selected from the group consisting of a bulk acoustic wave (BAW) device, a surface acoustic wave (SAW) device, and a Love mode device.

13. The method of claim 10 wherein each of the sensor coatings is made from a material selected from the group consisting of metal, metallic alloy, polymer, ceramic, carbon, nano-structure, or gold nano-particles.

14. The method of claim 10 wherein step (k) includes analyzing orthogonal physical properties.

15. The method of claim 10 which further includes;

(m) arranging an external electrode between one of the resonators and the external electrode in order to set up an electrical field;

(n) measuring the mass loss;

(o) integrating the results of the measurements into steps (k) and (l).

16. The method of claim 10 which further includes:

(m) applying a sensor coating capable of fluorescing on one of the resonators;

(n) arranging an optical source and an optical detector to probe the fluorescing sensor coating;

(o) measuring the fluorescence;

(p) integrating the results of the measurements into steps (k) and (l).

17. The method of claim 10 which further includes one or more of the following steps:

(m) measuring time;

(n) using a GPS receiver to ascertain location, including latitude, longitude, and altitude;

(o) measuring temperature;

(p) measuring humidity;

(q) measuring air speed and direction.

18. The method of claim 10 which further includes:

(m) means for activating an alarm when a hazardous biological and chemical agent is identified.

19. The sensor device of claim 1 wherein some of the electrodes of the resonators are coated with nano particles.

* * * * *